United States Patent [19]
Bennett et al.

[11] Patent Number: 5,628,329
[45] Date of Patent: May 13, 1997

[54] METHODS AND APPARATUS FOR OBTAINING AND MAINTAINING PENILE ERECTION

[75] Inventors: Boyd B. Bennett, 3717 Hilldale Rd., Louisville, Ky. 40222; Moseley C. Collins, West Plam Beach, Fla.

[73] Assignee: Boyd B. Bennett, Louisville, Ky.

[21] Appl. No.: 507,147

[22] Filed: Jul. 26, 1995

[51] Int. Cl.$^6$ ............................................. A61F 6/02
[52] U.S. Cl. .............................................. 128/842; 600/39
[58] Field of Search .............................. 128/842, 844, 128/918; 604/347–353; 600/38–40

[56] References Cited

U.S. PATENT DOCUMENTS 1,216,099 2/1917 Falck .................................... 600/39
2,868,192 1/1959 Dannen ................................. 600/39
5,246,015 9/1993 Baber ................................... 600/39
5,344,389 9/1994 Walsdorf ............................... 600/39

Primary Examiner—Michael A. Brown
Attorney, Agent, or Firm—Jack A. Kanz

[57] ABSTRACT

An elastic band with a tapered bore extending therethrough is positioned on the base of the penis for maintaining a penile erection. Flanges extend radially from the base of the band to stretch it and spread it sufficiently for application. When the stretching force is released the residual elastic force in the band constricts the base of the penis to restrict outflow of blood from the base of the penis. The elongated structure also provides physical support at the base of the penis as an aid in supporting a penis afflicted by Peyronie's disease or the like at the penis base.

20 Claims, 2 Drawing Sheets

METHODS AND APPARATUS FOR OBTAINING AND MAINTAINING PENILE ERECTION

This invention relates to assistance in obtaining and maintaining erection of the human penis for sexual intercourse. Particularly, it relates to elastic devices which constrict the base of the penis to prevent outflow of blood from the penis after erection is achieved and which assist in maintaining erection by supporting the base of the penis in individuals affected by localized defective tunica albuginea surrounding the corpora cavernosa.

Loss of the ability to maintain penile erection is common among human adults. In some cases the causes are psychological. In other cases the causes are physiological. Regardless of the cause, however, the desire to have intercourse is unaffected but intercourse is prevented or diminished by failure to obtain and/or maintain an erection.

The anatomical phenomena associated with erections are well known. The penis is composed of erectile tissue having a sponge-like structure containing spaces which accept blood. These spaces are fed by arterioles and are drained by discharge veins. Muscle fibers traverse the walls of the spaces and surround the discharge veins. When the penis is stimulated, arterioles feeding the spaces dilate, the muscle fibers around the spaces relax, and the muscles controlling the discharge veins contract. The spaces in the erectile tissue expand as blood is pumped therethrough at high pressure and the penis becomes rigid and erect. A natural erection thus consists of capturing and holding pressurized blood in the erectile tissues of the penis. Failure of the corpora cavernosa to expand and remain expanded, whether of physical or psychological origin, results in failure to obtain and/or maintain a proper erection.

One common physical cause of failure to obtain a proper erection is Peyronie's disease in which a localized portion of the corpora cavernosa (usually adjacent the base) fails to accept blood because of fibrotic scar or plaque. In such cases, the base of the penis fails to enlarge and thus, even if the reminder of the penis is enlarged, erection sufficient for vaginal penetration cannot be obtained because the flaccid base will not support the enlarged penis.

Surgical implants have been developed to produce artificial erection. Such implants are typically one or more expansible implanted sacs connected to a fluid-filled bulb which pumps fluid into the sac to simulate the natural process. Implanting artificial devices, however, can result in permanent destruction of nerves and blood vessel passages to such an extent that a natural erection can never again be obtained. Furthermore, implant techniques usually require hospitalization and the associated hospital and surgical expense can be substantial.

A device for maintaining an erection (known as a pubis ring) can be used when an erection can be developed but can not be maintained. The pubis ring is applied externally of the penis and keeps blood in the penis after it has been pressurized by natural reaction to sexual stimuli. This device is essentially a cord extending through a flexible sleeve with both ends emerging at a radial hole in the sleeve so that the sleeve forms a loop. The loop is positioned on the base of the penis when the erection is at its maximum and the cord then snubbed to trap the pressurized blood in the penis and maintain the erection. Use of the pubis ring requires dexterity to secure. Furthermore, focusing attention on the securing problem is often sufficiently distracting to cause the erection to be lost.

Another device used to maintain an erection (known as a male organ conditioner) comprises an elastic ring with loops on opposite sides. The loops are used to expand the ring so that it may be set on the root or base of the penis. When the loops are released the ring contracts to prevent outflow of blood and thus maintain the erection. However, the ring constricts only a narrow portion of the penis and does not force enough blood from the base of the penis into the unconstricted portion of the penis to enhance rigidity. Furthermore, the ring may serve to further weaken tissue at the base of the penis which has already been weakened by disease or defect and itself provides no physical rigidity or support.

In accordance with the present invention a penile erection device is provided which comprises an annular elastic band which defines a short open-ended cylinder. The inside surface is defined by a bore passing entirely through the cylindrical band along its longitudinal axis. A pair of flanges or grasping handles are joined to opposite sides of the band for imparting radially outwardly expanding forces which enlarge the band so it can be passed over an erect penis and positioned at its base. When the outward force is relieved the residual elastic constricting force in the band contracts on the penis to restrict the outflow of blood. Because of its truncated cylindrical shape the band also forces blood from the constricted length into the unconstricted length of the penis, thus enhancing rigidity along the full length of the penis and also provides physical support at the base of the penis. The distance defined by the axial length of the cylinder optimizes the quantity of blood forced into the unconstricted portion of the penis. Other features and advantages of the invention will become more readily understood from the following detailed description taken in connection with the appended claims and attached drawing in which:

Figure 1:
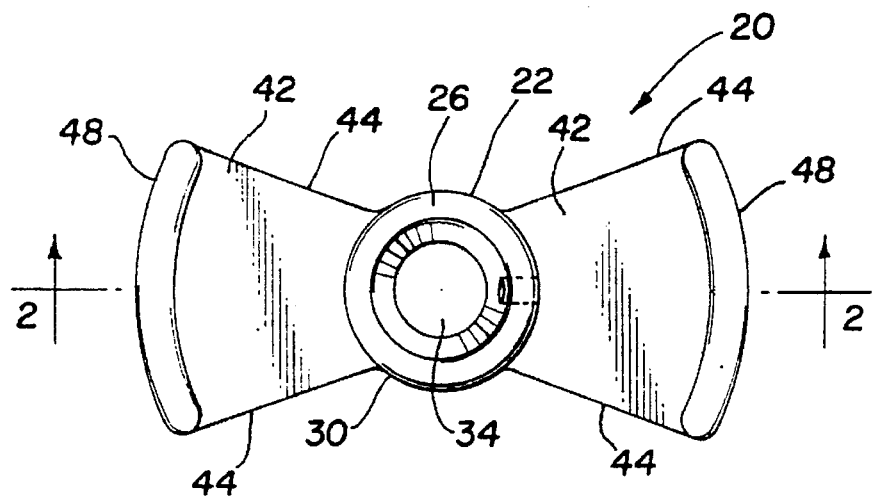
FIG. 1 is a top plan view of a presently preferred embodiment of the invention.
Figure 2:
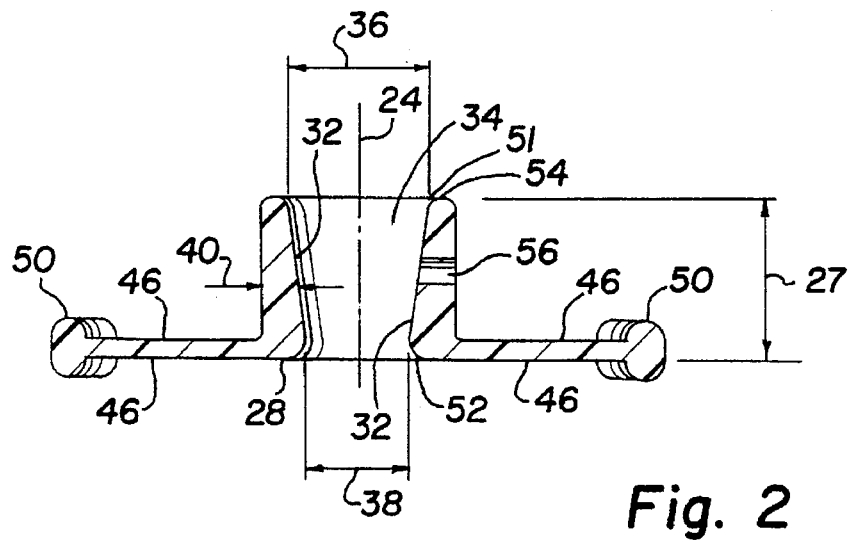
FIG. 2 is a cross-sectional view of the device of FIG. 1 taken through line 2—2.
Figure 3:
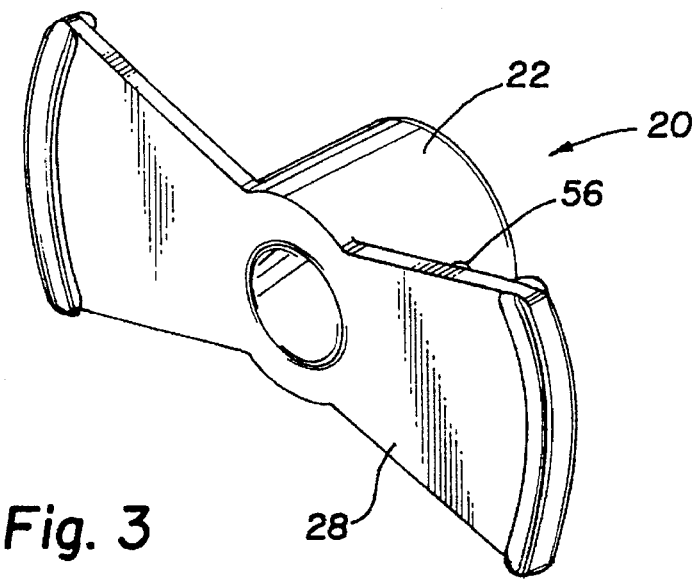
FIG. 3 is a perspective view of the device of FIG. 1.

A preferred embodiment of the invention (designated generally by the numeral 20) is illustrated in FIGS. 1-3. The device 20 comprises an annular band or tube 22 circular about a central longitudinal axis 24 forming a short or truncated cylinder. The band 22 is formed of elastic material such as natural rubber, synthetic rubber, silicone rubber or the like having a durometer number within the range of about fifteen (15) to about twenty-five (25). In the presently preferred embodiment the durometer number is about twenty (20). The top surface or first end 26 is spaced a predetermined distance or length 27 from the bottom surface or second end 28. The length 27 of the band or tube 22 is preferably about thirty (30) to about forty (40) millimeters as measured along the longitudinal axis 24 extending between the first end 26 and second end 28 with a length of about thirty-three (33) millimeters being preferred. In the presently preferred embodiment, the bore tapers uniformly from a first diameter at about the top surface to a second diameter at about the bottom surface to form a truncated or funnel-shaped cavity.

An outer or exterior surface 30 extends between the top surface 26 and the bottom surface 28. In the preferred embodiment the outer surface 30 is centered on the longitudinal axis 24 and maintains a substantially uniform diameter as it extends between the top surface 26 and the bottom surface 28. The bore 34 may have a substantially uniform diameter along its entire length 27, but a conical or funnel-shaped cavity (as illustrated in FIGS. 1 and 2) is preferred.

The bore 34 is coaxial with the longitudinal axis 24 and is thus concentric with the outer surface 30. As illustrated in FIG. 2, the bore 34 includes a first diameter or wide opening 36 at or near the top surface 26 and a second diameter or narrow opening 38 at or near the bottom surface 28. The first diameter 36 is larger than the second diameter 38 and the bore 34 tapers from the first diameter 36 to the second diameter 38. The diameter of the bore 34 is less than the diameter of the outer surface 30, thus defining a wall thickness 40 therebetween. The wall thickness 40, of course, depends on the respective diameters of the outer surface 30 and the bore 34 at any given point. Since the conical bore 34 diameter varies between the wide opening 36 and the narrow opening 38, the wall thickness 40 also varies.

Figure 4:
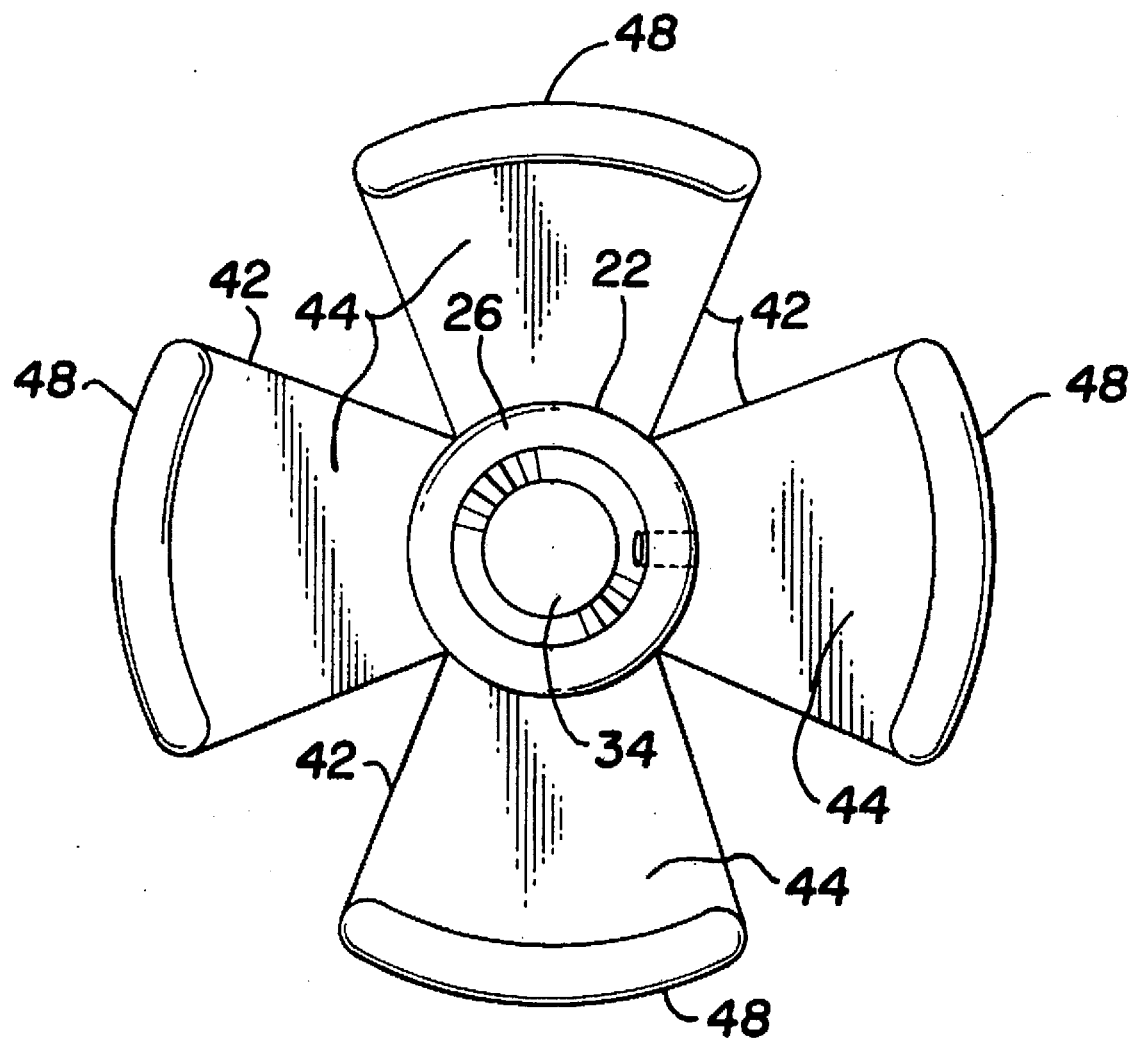
FIG. 4 is a top plan view of an embodiment which includes a second pair of flanges.

In the embodiment illustrated a first pair of flanges or grasping handles 42 is joined to the outer surface 30 nearer the first end 26 than the second end 28. The flanges 42 are preferably integrally formed with and are part of the band 22. The flanges 42 are substantially mirror images of each other and are located on diametrically opposite sides of the band 22. A second pair of flanges (not shown) to facilitate four-handed application and removal may be provided if desired. Such second pair of flanges would be spaced 180° apart and orthogonal to the first pair of flanges as illustrated in FIG. 4.

Each flange or grasping handle 42 comprises a web 44 extending radially outwardly from the band 22; a pair of oppositely disposed gripping surfaces 46; and an outer edge 48. In the presently preferred embodiment the webs 44 expand uniformly as they extend radially from the band 22, thus providing larger gripping surfaces 46. The terminal ends of webs 44 preferably include a reinforced bead 50 which is continuous along the full length of the outer edge 48 and extends above and below the opposed gripping surfaces 46.

The corner 52 of the inside surface 32 and the bottom surface 28 is made with a chamfer 51, as is the corner 54 of the inside surface 32 and the top surface 26. The term "chamfer" as used herein includes any geometry within the conventional meaning of the term and any other geometry relieving a corner including, without limitation, a rounded edge or the like.

If desired, a hole 56 may be provided which passes radially through the wall thickness 40 to accommodate a hypodermic needle (not shown) or the like. The hole 56 is located as shown in FIGS. 1 and 3 for illustrative purposes only. In practice, the hole 56 may be positioned anywhere in the band 22 which enables the user to access it for its intended purpose and/or which identifies a required position for insertion.

To apply the device 20, the user imparts opposing forces on flanges 42 to radially stretch and enlarge the internal diameter of the band 22. When the bore 34 is sufficiently enlarged, the penis is inserted into the bore 34 through the second diameter 38. The device 20 is then positioned encircling the base of the penis. The chamfer 51 at corner 52 facilitates entry of the penis into the second diameter 38 and relieves discomfort which would otherwise result from a sharp edge. The chamfer 51 at corner 54 serves similar purposes. When the flanges 42 are released, the residual elastic force in the band 22 constricts on the base of the penis and restricts the outflow of blood sufficiently to maintain the erection. The tapered axial length 27 of the device 20 also forces a quantity of blood in base of the penis toward and into the unconstricted portion thereof to increase rigidity.

The preferred conical bore or funnel cavity 34 provides sequentially reducing pressure from the second end 28 to the first end 26 along the penis base to enhance the movement of blood to the unconstricted portion of the penis.

The elongated cylindrical device of the present invention is particularly effective in providing support for a penis affected by Peyronie's disease at the base. Since in many cases of Peyronie's disease only a small portion of the penis adjacent the base is affected, the cylindrical device of the invention can be used as a physical support bridging the affected portion of the penis and thus maintaining the enlarged penis erect and enlarged.

In some disorders (including, sometimes, Peyronie's disease) an erection-enhancing substance which aids in obtaining and/or maintaining erection (or which is applied as treatment for affected tissue) is injected directly into the penis hypodermically. In most cases the substance is injected into the corpora cavernosa adjacent the penis base at about the two o'clock position. One such erection-enhancing substance is Prostaglandin E-1. The device of the present invention can be particularly adapted to assist in proper and timely injection of erection-enhancing substances by including a hole passing radially through the wall of the cylindrical or tubular device at about the two o'clock position on the device which corresponds with the appropriate injection point on the penis when the cylindrical device is properly applied. Thus the device of the invention may be applied to the penis as described above and, after the band 22 is in place, a vasoactive dilator (or other desired substance) can be injected into the penis through the radial hole 56 using a hypodermic needle or the like. The cylindrical band 22 thus not only acts as a constrictive cylindrical support which braces the weakened base of the penis, it acts as a guide to correctly locate the proper point for hypodermic injection and retard outflow of blood from the penis.

The shape and size of the device of the invention may, of course, be varied as desired and as needed to compensate for the particular affliction of the user. While the invention has been described with reference to only several specific applications, various other conditions which prohibit erection or proper maintenance of erection can be overcome or at least partially treated by various embodiments of the principles of the invention disclosed.

From the foregoing it will be recognized that the principles of the invention maybe employed in various arrangements to obtain the benefit of the many advantages and features disclosed. It is to be understood, therefore, that even though numerous characteristics and advantages of the invention have been set forth together with the details of the structure and function of the invention, this disclosure is to be considered illustrative only. Various changes and modifications in detail, especially in matters of size, shape and arrangement of parts, may be made without departing from the spirit and scope of the invention as defined by the appended claims.

What is claimed:

1. A unitary device for maintaining penile erection comprising:
   (a) an elastic annular band having a substantially cylindrical outer surface extending a predetermined distance from a bottom end to a top end and having an inside surface defined by a central bore extending through said band; and
   (b) a first pair of flanges extending from the outer surface of said band generally diametrically opposite each other for imparting a radially outward stretching force to said band to enlarge said bore sufficiently for said band to be positioned on the base of a penis such that when the stretching force is relieved a residual elastic force in said band restricts the outflow of blood from the penis and urges blood in the base thereof into the unconstricted length of the penis.

2. A device as defined in claim 1 wherein said bore tapers from a first diameter at the top end to a smaller diameter at the bottom end.

3. A device as defined in claim 1 wherein the top end is spaced from the bottom end a distance of from about thirty millimeters to about forty millimeters.

4. A device as defined in claim 3 wherein the top end is spaced from the bottom end a distance of about thirty-three millimeters.

5. A device as set forth in claim 1 wherein said flanges expand with distance from said band and terminate in an expanded bead.

6. A device as defined in claim 1 wherein the elastic material of said annular band has a durometer number within the range of about 15 to about 25.

7. A device as defined in claim 6 wherein the durometer number is 20.

8. A device as defined in claim 1 including a hole of a size sufficient to accommodate a hypodermic needle passing radially through said elastic band.

9. A device as defined in claim 1 including a second pair of flanges extending from the outer surface generally diametrically opposite of each other and in an orthogonal relationship with said first pair of flanges.

10. A device for maintaining penile erection comprising:

(a) an elastic tube having first and second ends, a cylindrical exterior surface substantially concentric about a central longitudinal axis, and an interior funnel-shaped cavity extending therethrough having an opening at the first end thereof which is greater than the opening at the second end; and (b) a first pair of oppositely disposed grasping handles extending from said tube nearer the second end than the first end and adapted to be pulled radially outwardly to enlarge said tube sufficiently to pass over an enlarged penis so that said tube can be positioned at the base of the penis to constrict the base of the penis, thereby restricting the outflow of blood from the penis and urging blood in the base thereof into the unconstricted length thereof when said handles are released.

11. A device as defined in claim 10 wherein the length of said tube is about thirty millimeters to about forty millimeters.

12. A device as defined in claim 11 wherein the length of said tube is about thirty-three millimeters.

13. A device as defined in claim 10 wherein the elastic material of said tube has a durometer number within the range of about 15 to about 25.

14. A device as defined in claim 13 wherein the durometer number is about 20.

15. A device as defined in claim 10 including a hole of a sufficient size to accommodate a hypodermic needle passing radially through said tube.

16. A device as defined in claim 10 including a second pair of handles generally diametrically opposite of each other and in an orthogonal relationship with said first pair of handles.

17. A method of obtaining and maintaining a penile erection comprising the steps of:

(a) supporting the base of the penis with a constrictive elastic cylinder which restrains outward blood flow at the base of the penis; and (b) injecting an erection-enhancing substance into the penis with an injection device passing substantially radially through said elastic cylinder.

18. A method as set forth in claim 17 wherein said erection-enhancing substance is Prostaglandin E-1.

19. A method as set forth in claim 17 wherein said erection-enhancing substance is injected into the penis at about the two o'clock position.

20. A method as set forth in claim 17 wherein said erection-enhancing substance is injected directly into the corpora cavernosa.

* * * * *